United States Patent [19]

Sun

[11] Patent Number: 4,979,499
[45] Date of Patent: Dec. 25, 1990

[54] STERILE DISPOSABLE LINGUIFORM LARYNGOSCOPE BLADE SHEATH

[76] Inventor: William Y. Sun, 401 N. Armistead St., Apt. 104, Alexandria, Va. 22312

[21] Appl. No.: 357,274

[22] Filed: May 26, 1989

Related U.S. Application Data

[63] Continuation-in-part of Ser. No. 917,691, Sep. 16, 1986, Pat. No. 4,834,077, which is a continuation-in-part of Ser. No. 713,694, Mar. 3, 1985, abandoned.

[51] Int. Cl.⁵ ............................................. A61B 1/06
[52] U.S. Cl. ...................................... 128/11; 128/16
[58] Field of Search ................... 128/10, 11, 200.26, 128/3, 15, 16, 17

[56] References Cited

U.S. PATENT DOCUMENTS

| | | | |
|---|---|---|---|
| 3,426,749 | 2/1969 | Jephcott | 128/11 |
| 3,851,642 | 12/1974 | McDonald | 128/18 |
| 4,579,108 | 4/1986 | Bauman | 128/10 |
| 4,874,077 | 5/1989 | Sun | 128/11 |

Primary Examiner—Edward M. Coven
Assistant Examiner—Mark S. Graham
Attorney, Agent, or Firm—Clyde I. Coughenour

[57] ABSTRACT

A sterile, disposable laryngoscope blade sheath for use in the intubation process is disclosed. The sheath either provides for or permits the laryngoscope structure to perform the desired or designed functions. Such functions may be, for example, the manipulation of the epiglottis while maintaining the tongue positioned. This is accomplished by either providing an opening in the end of a rigid sheath for the shaped blade end to project through, or by shaping the rigid sheath so that it can perform the function using or independent of the blade end shape, or by providing a resilient end section that assumes or conforms to the shape of the blade.

14 Claims, 1 Drawing Sheet

U.S. Patent    Dec. 25, 1990    4,979,499

STERILE DISPOSABLE LINGUIFORM LARYNGOSCOPE BLADE SHEATH

CROSS REFERENCE

This invention is a Continuation-in-Part of applicant's application Ser. No. 06/917,691 filed 16 Sept. 1986, now U.S. Pat. No. 4,834,077 issued 30 May 1989; which is a Continuation-in-Part of application Ser. No. 06/713,694 filed 3 Mar. 1985 now abandoned.

BACKGROUND OF THE INVENTION

1. Field of the Invention

The invention is to a sheath for use with laryngoscope blades. These blades are used by physicians and others for inspection of patients' throats, intubation procedures, and for manipulation of body parts.

The blades in use are shaped for viewing and manipulation of body parts, but are too narrow and too slippery to hold and control the tongue. As a result, the epiglottis is difficult to visualize and it is difficult to insert the endotracheal tube into the trachea.

In the event of cardiac or respiratory arrest, an endotracheal tube must be inserted promptly to avoid irreversible brain damage.

The invention helps to overcome the above-mentioned problems by positioning, or restraining, the tongue while performing or permitting the blade to perform designed functions such as manipulation of the epiglottis.

2. Description of the Prior Art

Many prior art devices use attachments to a laryngoscope for intubation purposes. These blades are commercially available under such names as Macintosh, Wisconsin, and Miller Laryngoscope Blades. These attachments and laryngoscope instruments are frequently formed in shapes designed to perform specific functions. Examples are instruments designed to be used on the epiglottis or epiglottis fold. The instruments to be used in a patient's epiglottis fold are usually provided with an elongated cylindrical or bulbous end section that extends perpendicularly across the distal or tip end of the instrument. This type blade can be seen in U.S. Pat. No. 4,114,609 issued 19 Sept. 1978 to John A. Moses. The instruments used to manipulate the entire exposed portion of the epiglottis and other body parts are often provided with a bulbous or non-bulbous end section that extends around the curved distal or tip end of the instrument blade. This type of curved blade is shown, for example, by W. H. Allyn in U.S. Pat. No. 2,070,820 issued 16 Feb. 1937.

Included in the prior art is the use of a sterile disposable cover. The patent to J. A. Jephcott, U.S. Pat. No. 3,426,749, issued 11 Feb. 1969 is an example of a cover used with a laryngoscope. The only patent known that is designed to support the tongue using a sheath is that issued to applicant as set forth in the above CROSS-REFERENCE.

Intubation can be a difficult procedure because all the commonly used laryngoscope blades presently on the market are narrow and become slippery on contact with the tongue. Prior art laryngoscope blade covers or sheaths of the flexible type will not support and control the position of the tongue. Prior art sheaths of the rigid type, as set forth in applicant's prior application, obstruct and will not permit the blade ends to perform their designed function.

SUMMARY OF THE INVENTION

There are disclosed shaped self supporting sheaths that are wide enough to support and hold the tongue stable while positioned on a laryngoscope blade, permitting viewing and manipulation of body parts. The sheath is rigid enough to be both self supporting and capable of supporting the weight of the tongue and forces exerted by it. This function may be performed with a sheath having either a smooth or textured surface. The sheath is provided with (a) an opening that permits the shaped blade end to protrude through, or (b) a resilient end section that will take the shape of the blade end, or (c) a shaped end section to perform the desired functions. While the sheath is rigid enough to retain its shape against the weight of and pressure exerted by the tongue, it has enough resilience to deform slightly for forced insertion of odd-shaped hard stainless steel laryngoscope blades. The sheaths are inexpensive and can be manufactured in different sizes and shapes to fit different size mouths and perform different functions.

Accordingly, it is the object of the present invention to provide:

a sheath that positions and controls the tongue while permitting a shaped laryngoscope blade to perform its designed function;

a sheath that positions and controls the tongue with one section, while conforming to the shape of a laryngoscope blade with another;

a sheath that positions and controls the tongue while shaped and structured to manipulate body parts;

a sheath that positions and controls the tongue and manipulates body parts while guiding light and other means to the area to be manipulated;

a sheath that positions and controls the tongue and manipulates body parts while preventing passage of body and other fluids;

a sheath that lifts the tongue easily with quicker smoother intubation that decreases complications, infections and death rates.

BRIEF DESCRIPTION OF THE DRAWINGS

These and other features and advantages of the invention, and a complete understanding thereof, will be better understood and appreciated from the following disclosure in conjunction with the accompanying drawings wherein.

BRIEF DESCRIPTION OF THE PREFERRED EMBODIMENTS

Figure 1:
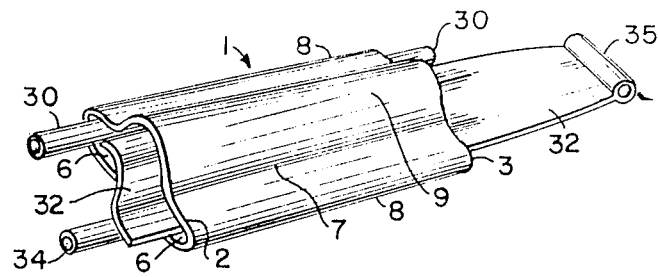
FIG. 1 is a perspective view of a preferred embodiment of the sheath of the invention.

In accordance with the present invention, a sterile disposable laryngoscope blade sheath 1 is provided. The sheath has a proximal end 2 and distal end 3 with a channel 6 through which most standard laryngoscope blades will fit or can be forced. The lateral edges 8 are made sufficiently wide so that the whole tongue may be lifted during the intubation process. The curved portions 7 form a rim that helps hold the tongue stable during intubation. The curved upper face 9 adds strength and greater support for the tongue.

The specific shapes shown are illustrative only. The channel 6 may be shaped or designed to accommodate any shape blade 32,33,37 desired. The primary function of the sheath is to support and control the tongue while any of the various shape laryngoscope blades are used. To perform this function the sheath is rigid in that it is capable of supporting the tongue and any pressure that can be generated by it, while being capable of small distortions that may be necessary for passage of different shape blades, usually made of non-deformable stainless steel. The sheath is rigid enough to support the tongue, even if the blade is only inserted into one side of the sheath, such as depicted in FIGS. 1 and 3.

Referring to FIG. 1, there is shown a rigid sheath 1 that is open at both the proximal end 2 for the introduction of the blade 32, and the distal end 3, for the passage therethrough of the shaped blade end, shown as a bulbous cylindrical means 35. With this configuration, the function of the sheath 1, supporting and controlling the tongue, and the blade end 35, manipulating body parts, can both be accomplished in concert. The open ends also permit passage of an illumination means 30, tube 34, or other elements.

Figure 2:
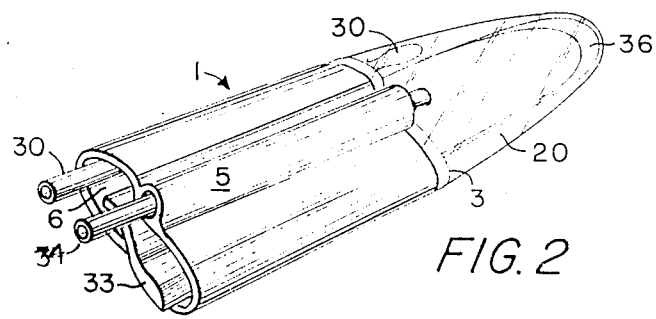
FIG. 2 is a view similar to FIG. 1 with a resilient extension attached to the distal end of the sheath.

Referring to FIG. 2, there is shown a rigid sheath 1 that has attached to the distal end 3 thereof a resilient extension 20. With this structure, the blade can be inserted through the rigid sheath channel 6 with the end of the blade extended into the resilient extension 20. The resilient extension yields or stretches to take on the size and shape of the blade 33. With this extension 20, any specific shape blade end can be used with the rigid sheath and still have the blade perform the function for which it was designed. The resilient extension may be transparent so as to transmit light from a light source 30, or can be provided with transparent areas for that purpose. With this type sheath the blade can be maintained sterile by preventing contact between the blade and body parts. The resilient extension can be secured to the rigid sheath by crimping, welding, adhesives, fusion or any of the other commonly used joining or bonding means. In the alternative, a transparent resilient sheath can be used, similar to that disclosed by J. A. Jephcott. The rigid sheath as shown in FIG. 1 can be inserted, in part or totally, within the resilient sheath to provide essentially the structure shown in FIG. 2. An external guideway 5 can be provided for tubes or other elements, if desired.

Figure 3:
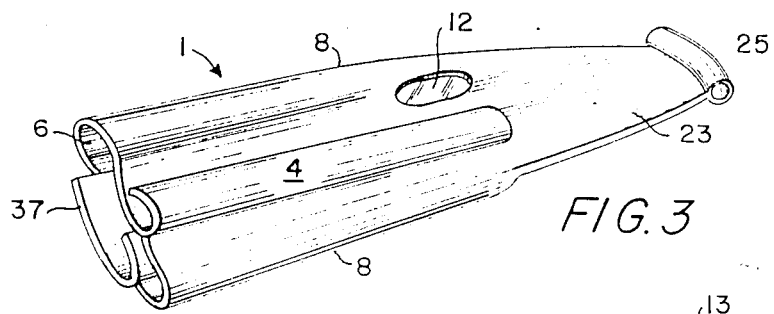
FIG. 3 is a view similar to FIG. 1 with the rigid sheath extended and shaped at the distal end.
Figure 4:
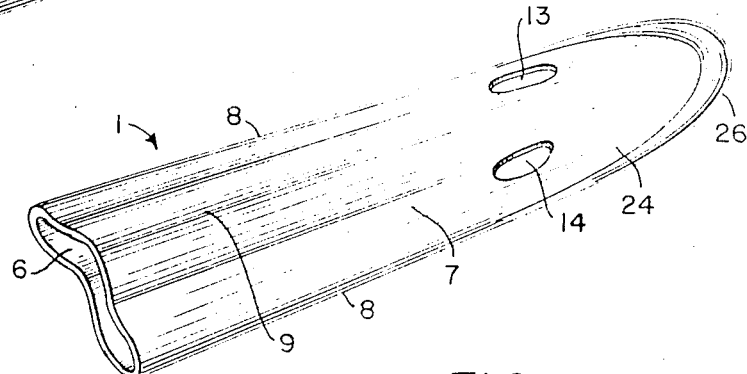
FIG. 4 is a view similar to FIG. 3 with a different shape rigid extension on the distal end of the sheath.

Referring to FIGS. 3 and 4, there are shown rigid sheaths 1 that are extended or have rigid extensions 23 and 24 thereon. The rigid extensions may have a cylindrical end 25, or an arcuate bulbous end 26, or any other desired shape. These shapes will in general be the same as those provided on laryngoscope blades designed to perform specific functions. By use of these rigid sheaths any type laryngoscope blade can be used with the sheath, including those having no specific blade end shape. Several sheaths can be used, in the alternative or in sequence, to perform different functions with one blade. With these sheaths the need for plural expensive special-purpose stainless steel blades is eliminated.

The embodiment of FIG. 3 protects the blade from contamination during use by preventing contact between the blade and body parts. A transparent area 12 is provided for illumination. An external guideway 4 is provided for guidance of a tube or other means. The embodiment of FIG. 4 permits the sheath to act as a guideway for illumination means, tubes or other elements, as well as performing the restraint of the tongue and manipulation of body parts. The sheath is provided with openings 13 and 14 that permit a passage for the illumination means, tubes or other means.

It is believed that the construction, operation and advantages of this device will be apparent to those skilled in the art. It is to be understood that the present disclosure is illustrative only and that changes, variations, substitutions, modifications and equivalents will be readily apparent to one skilled in the art, and that such may be made without departing from the spirit of the invention as defined by the following claims.

What I claim is:

1. A sterile disposable linguiform sheath, for mounting on a fixed length laryngoscope blade having a width and a shaped distal end for manipulation of a body part, said sheath having a proximal end and a distal end with a fixed distance there-in-between and lateral edges and containing a longitudinal channel with an orifice adapted for insertion of said laryngoscope blade into said proximal end, said sheath lateral edges being wider than said blade width and capable of extending beyond said blade width a sufficient distance to support a tongue and shaped to support a tongue, said sheath including a rigid material such that it is self supporting and capable of maintaining its shape against the weight of and force exerted by the tongue so as to support the tongue without slippage during use, said distal end, terminating in essentially the same size and shape as that of the proximal end including exposure of and access to said longitudinal channel, said distance between said sheath proximal and distal ends being less than the length of said laryngoscope blade received therein such that said sheath can terminate short of the length of said shaped laryngoscope blade received therein so that the tongue may be supported and controlled by said sheath while permitting said shaped laryngoscope blade to extend through said longitudinal channel and beyond said sheath distal end to manipulate a body part.

2. A sterile disposable linguiform sheath as defined in claim 1 wherein said orifice is large enough to permit illumination means and a tube to be inserted into and guided through said sheath longitudinal channel while said laryngoscope blade is received therein.

3. A sterile disposable linguiform sheath having a proximal and a distal end for mounting on a laryngoscope blade having a width and a shaped distal end, said sheath containing a longitudinal channel with an orifice adapted for the insertion of said laryngoscope blade into said proximal end, said sheath lateral edges being further apart than the width of said laryngoscope blade so that they can extend beyond said laryngoscope blade and said edges being shaped to support a tongue, said sheath including a rigid material such that it is self-supporting and capable of maintaining its shape against the weight of and force exerted by the tongue so as to support the tongue without slippage during use, the distal end of said sheath provided with means that will permit manipulation of a body part wherein said means at the sheath distal end is a resilient means that will permit entry of said shaped laryngoscope blade end and that will stretch to take on the shape of said laryngoscope blade end.

4. A sterile disposable linguiform sheath as defined in claim 3 wherein said resilient means is provided with a transparent area that will permit light to shine therethrough.

5. A sterile disposable linguiform sheath as defined in claim 3 wherein said resilient means is transparent permitting light to shine therethrough.

6. A sterile disposable linguiform sheath as defined in claim 3 wherein said resilient means and said sheath are joined so as to seal out body and other fluids.

7. A sterile disposable linguiform sheath as defined in claim 3 wherein said sheath is provided with a guideway on an outer surface of said rigid sheath.

8. A sterile disposable linguiform sheath as defined in claim 3 wherein said resilient means extends over and surrounds said rigid linguiform sheath.

9. A sterile disposable linguiform sheath as defined in claim 8 wherein the resilient means is transparent so as to permit light to shine therethrough.

10. A sterile disposable linguiform sheath for mounting on a laryngoscope blade having a distal end of standard shape, said sheath having a proximal end and a distal end and lateral edges and containing a longitudinal channel with an orifice adapted for the insertion of said laryngoscope blade into said sheath proximal end, said channel terminating short of said sheath distal end and able to accommodate any of said standard shaped laryngoscope blade distal ends, said sheath lateral edges being wider than and shaped to extend beyond said laryngoscope blade in opposite directions and shaped to support the tongue, said sheath including a rigid material such that it is self-supporting and capable of maintaining its shape against the weight of and force exerted by the tongue so as to support the tongue without slippage during use, said channel terminating far enough from said sheath proximal end to fit over and beyond said distal end of said laryngoscope blade used with said sheath, the distal end of said sheath provided with means that will permit manipulation of a body part wherein said means at said sheath distal end is in the form of a rigid extension of said rigid sheath material extending a distance beyond said channel, said sheath rigid distal extension being narrower than the distance between said sheath lateral edges, and said sheath rigid distal extension terminating in a rigid cylindrical or bulbous extremity shaped for the manipulation of a body part such that the sheath can be mounted onto and perform its desired function irrespective of the shape of the laryngoscope blade it is mounted on.

11. A sterile disposable linguiform sheath as defined in claim 10 wherein said sheath is provided with a transparent area that will permit light to shine therethrough.

12. A sterile disposable linguiform sheath as defined in claim 10 wherein said sheath is provided with an external guideway.

13. A sterile disposable linguiform sheath as defined in claim 11 wherein said sheath is constructed so as to seal out body and other fluids.

14. A sterile disposable linguiform sheath as defined in claim 10 wherein said rigid sheath channel serves as a guideway and said sheath is provided with an opening adjacent said shaped distal end extremity for the passage of light or for the passage of other means.

* * * * *